US008156933B2

(12) United States Patent
Raghuprasad

(10) Patent No.: US 8,156,933 B2
(45) Date of Patent: Apr. 17, 2012

(54) CLOUD NEBULIZER

(76) Inventor: Puthalath Koroth Raghuprasad, Odessa, TX (US)

( * ) Notice: Subject to any disclaimer, the term of this patent is extended or adjusted under 35 U.S.C. 154(b) by 1330 days.

(21) Appl. No.: 11/425,533

(22) Filed: Jun. 21, 2006

(65) Prior Publication Data

US 2007/0295328 A1 Dec. 27, 2007

(51) Int. Cl.
*A61M 11/00* (2006.01)
*B05B 17/06* (2006.01)

(52) U.S. Cl. .............................. 128/200.16; 128/200.14

(58) Field of Classification Search ............. 128/200.14, 128/200.16, 200.21, 200.23, 200.11, 203.12, 128/203.15, 203.16, 203.19, 203.21, 203.23, 128/203.25, 203.26, 204.14, 204.15
See application file for complete search history.

(56) References Cited

U.S. PATENT DOCUMENTS

| | | | | | |
|---|---|---|---|---|---|
| 4,094,317 | A | | 6/1978 | Wasnich | |
| 4,113,809 | A | | 9/1978 | Abair et al. | |
| 4,319,155 | A | | 3/1982 | Nakai et al. | |
| 4,358,935 | A | * | 11/1982 | Losert et al. | 62/188 |
| 4,850,534 | A | | 7/1989 | Takahashi et al. | |
| 4,961,885 | A | | 10/1990 | Avrahami et al. | |
| 5,170,782 | A | | 12/1992 | Kocinski | |
| 5,176,856 | A | | 1/1993 | Takahashi et al. | |
| 5,186,164 | A | * | 2/1993 | Raghuprasad | 128/200.14 |
| 5,217,165 | A | | 6/1993 | Takahashi et al. | |
| 5,299,739 | A | | 4/1994 | Takahashi et al. | |
| 5,312,281 | A | | 5/1994 | Takahashi et al. | |
| 5,355,872 | A | * | 10/1994 | Riggs et al. | 128/200.21 |
| 5,388,571 | A | * | 2/1995 | Roberts et al. | 128/203.12 |
| 5,549,102 | A | | 8/1996 | Lintl et al. | |
| 5,551,416 | A | | 9/1996 | Stimpson et al. | |
| 5,865,171 | A | * | 2/1999 | Cinquin | 128/203.12 |
| 5,908,158 | A | * | 6/1999 | Cheiman | 239/102.2 |
| 6,152,383 | A | * | 11/2000 | Chen | 239/102.2 |
| 6,748,944 | B1 | | 6/2004 | DellaVecchia et al. | |
| 2003/0015195 | A1 | | 1/2003 | Haaije de Boer et al. | |
| 2003/0230303 | A1 | * | 12/2003 | Nichols et al. | 128/200.14 |
| 2005/0081845 | A1 | | 4/2005 | Barney et al. | |
| 2005/0123483 | A1 | | 6/2005 | Gamard et al. | |
| 2006/0213508 | A1 | * | 9/2006 | Murray et al. | 128/200.16 |

FOREIGN PATENT DOCUMENTS

| | | |
|---|---|---|
| AU | 4398689 | 5/1990 |
| EP | 1190729 | 3/2002 |
| GB | 1069048 | 5/1967 |
| GB | 1270700 | 4/1972 |
| JP | 57-050570 | 3/1982 |
| JP | 62-215852 | 9/1987 |
| JP | 02-243166 | 9/1990 |
| JP | 04-215765 | 8/1992 |
| JP | 05-068711 | 3/1993 |
| JP | 5-123401 | 5/1993 |
| JP | 07-231938 | 9/1995 |

* cited by examiner

*Primary Examiner* — Kristen Matter
(74) *Attorney, Agent, or Firm* — David L King

(57) ABSTRACT

A nebulizer apparatus according to the present invention has an enclosure including a primary chamber of ambient air, a medicant chamber and a secondary chamber. The secondary chamber is for containing water and includes an ultrasonic transducer and is in communication with the primary chamber. The apparatus further has a first switch for activating pump means for evacuating air from the primary chamber after which the transducer is activated for a predetermined time. The pump stops after a predetermined pressure is achieved. The apparatus has a valve that opens allowing a dose of powdered medicine in the medicant chamber to move into the vapor-rich primary chamber to seed and form a cloud laden with medicine. A mouthpiece is attached to said primary chamber to allow the patient to suck and inhale the cloud. The mouthpiece may further include a one way valve that seals the mouthpiece during evacuation and upon the patient sucking the tubing of the mouthpiece the valve opens to allow the cloud to be inhaled.

14 Claims, 3 Drawing Sheets

CLOUD NEBULIZER

TECHNICAL FIELD

The present invention relates to a new and improved nebulizer, more particularly one designed to efficiently administer medications.

BACKGROUND OF THE INVENTION

Nebulizers can be used to deliver medications which are inhaled as an aerosol laden with the medicine over a delivery time of about 20 to 30 minutes. The use of nebulizers is found in the treatment of asthma or bronchitis or other respiratory related diseases. An attending respiratory technician, medical assistant or physician is required to insure the dosage is properly inhaled.

The length of time to administer the medications is quite long and therefore costly as well as uncomfortable for the patient.

Aerosol mist production makes use of an ultrasonic nebulizer to produce an aerosol mist for creating a humid environment and delivering drugs to the lungs.

Ultrasonic nebulizers function by transmitting ultrasound waves of sufficient energy through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine mist.

Aerosol mists produced by ultrasound are preferred because a heating element is not required to generate water vapor or mist and a smaller particle size of the aerosol can be obtained with the ultrasonic waves.

Most of the ultrasonic nebulizers currently in use today provide medications that are in a liquid form or a colloidal liquid suspension of particles. U.S. Pat. No. 4,094,317 patent entitled "Nebulizer System"; U.S. Pat. No. 5,551,416 "Nebulizer and Nebulizer Control System" and US 2005/0081845 A1 entitled "Breath Enhanced Ultrasonic Nebulizer and Dedicated Dose Ampoule" are examples of such devices.

US 2003/0015195 A1 published on Jan. 3, 2003; entitled "Powder Formulation Distinguishing Systems and Method for Dry Powder Inhalers" and US 2005/0123483 show inhaler type devices.

Dr. Raghuprasad, the inventor of a "Mist Inhaler" described in U.S. Pat. No. 5,186,164 discussed a novel way to generate a vapor which is condensed by a powder containing medications into a cloud of very fine particles that can be inhaled deep into a patient's lungs. As described the inhaler includes an enclosure, preferably a transparent container, which enables the patient to observe the formation of the cloud. The cloud is formed because of the provision within the enclosure of the proper pressure, moisture content, temperature, and a dust-like powder that is actually the medication and which seeds the cloud. A heater is placed adjacent to a liquid to cause the liquid to heat and vaporize. A small pump reduces the pressure within the container only the amount required to achieve the proper conditions for the cloud formation. A liquid is placed in a liquid containing part of the container. The patient actuates the starting mechanism and the pump partially evacuates the transparent container; then the heating element commences vaporizing the water, after which suitable medication powder flows into the transparent container, and seeds the cloud. The cloud should form at the instant the powdered medication is introduced into the transparent container. This is the signal for the patient to inhale the cloud.

This prior art device, while effective as an inhaler, did require a heater to be placed adjacent to the liquid to heat and vaporize the liquid. This pre-heating involves a small time delay and adds to the complexity of the inhaler as an additional cooling coil is required.

Accordingly it is desirable to provide a rapid responding nebulizer device that needs no heater, but can still accomplish a dispersion of dry powder medications or even oil soluble medicines in a very rapid manner.

It is further desirable to enable the patient to inhale all of the medication in as short as one or two breaths rather than the several minutes, typically 20 to 30 minutes required of currently available nebulizers.

These beneficial features are provided in the device of the present invention described as follows.

SUMMARY OF THE INVENTION

A nebulizer apparatus according to the present invention has an enclosure including a primary chamber of ambient air, a vented medicant chamber and a secondary chamber. The secondary chamber is for containing water and includes an ultrasonic transducer and is in communication with the primary chamber. The apparatus further has a first switch for activating a pump means for evacuating air from a primary chamber followed by the activation of the transducer for a predetermined time. The pump stops after a predetermined pressure is achieved. A valve opens allowing a dose of powdered medicine in the vented medicant chamber to move into the vapor-rich primary chamber to seed and form a cloud laden with medicine. The valve can be spring loaded or switch activated A mouthpiece is attached to said primary chamber by tubing to allow the patient to suck and inhale the cloud. The mouthpiece preferably has a one way valve located near the chamber that freely opens upon the sucking by the patient.

BRIEF DESCRIPTION OF THE DRAWINGS

The invention will be described by way of example and with reference to the accompanying drawings in which.

DETAILED DESCRIPTION OF THE INVENTION

Figure 1:
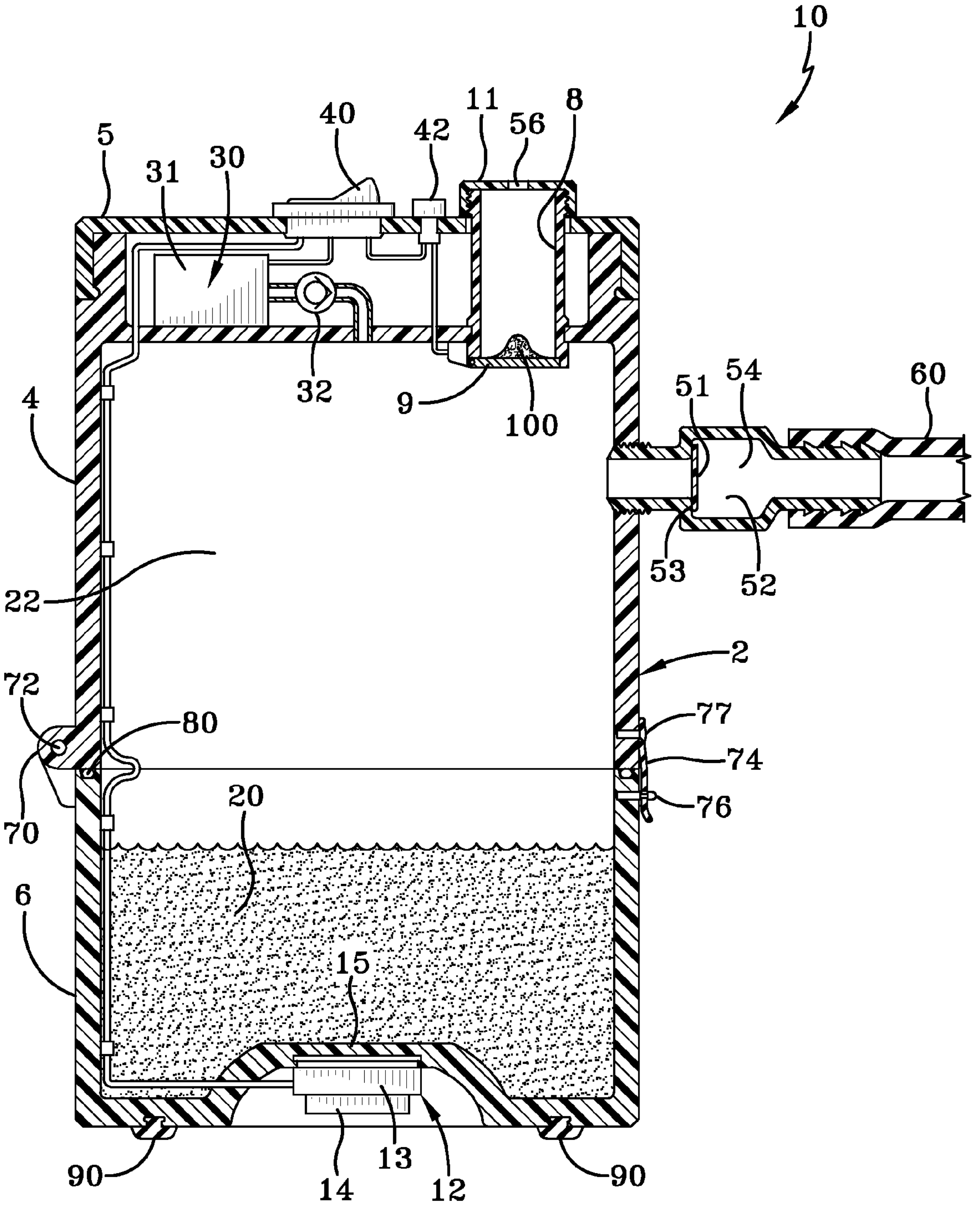
FIG. 1 is a cross sectional view of the nebulizer according to the present invention.

With reference to FIG. 1 a nebulizer apparatus 10 is shown in cross sectional view. The nebulizer has an enclosure 2. The enclosure 2 includes a primary chamber 4 initially filled with ambient air 22 and a secondary chamber 6. The secondary chamber 6 is open to and located below the primary chamber 4. Internal to the secondary chamber is an ultrasonic transducer 12, the transducer 12 is preferably a piezoelectric device 14 having a vibration amplification plate 13 in contact with a mist generating cover means 15 to generate a fog or fine mist of water vapor when activated. The secondary chamber 6 is filled or partially filled with water 20 as shown.

On the upper portion or top 5 of the primary chamber 4 is a vented medicant chamber 8 always vented to the atmosphere, but sealed from the primary chamber 4 of the enclosure 2. The medicant chamber 8 has a movable end closure or valve 9 which when opened provides a passage for the medicant dosage 100 to enter the primary chamber 4. Typically the dosage is very small, usually substantially less than 1 milligram, typically 50 to 200 micrograms. As shown in FIG. 1 the end closure or valve 9 is in the closed position. A screw on cap 11 is tightly fastened to the vented medicant chamber 8. The cap 11 is removed to add the dosage and then screwed back into place prior to initiating the administration of a treatment. The cap has a small air vent opening 56 allowing atmospheric air to enter the primary chamber 4 when the valve 9 opens.

Figure 2:
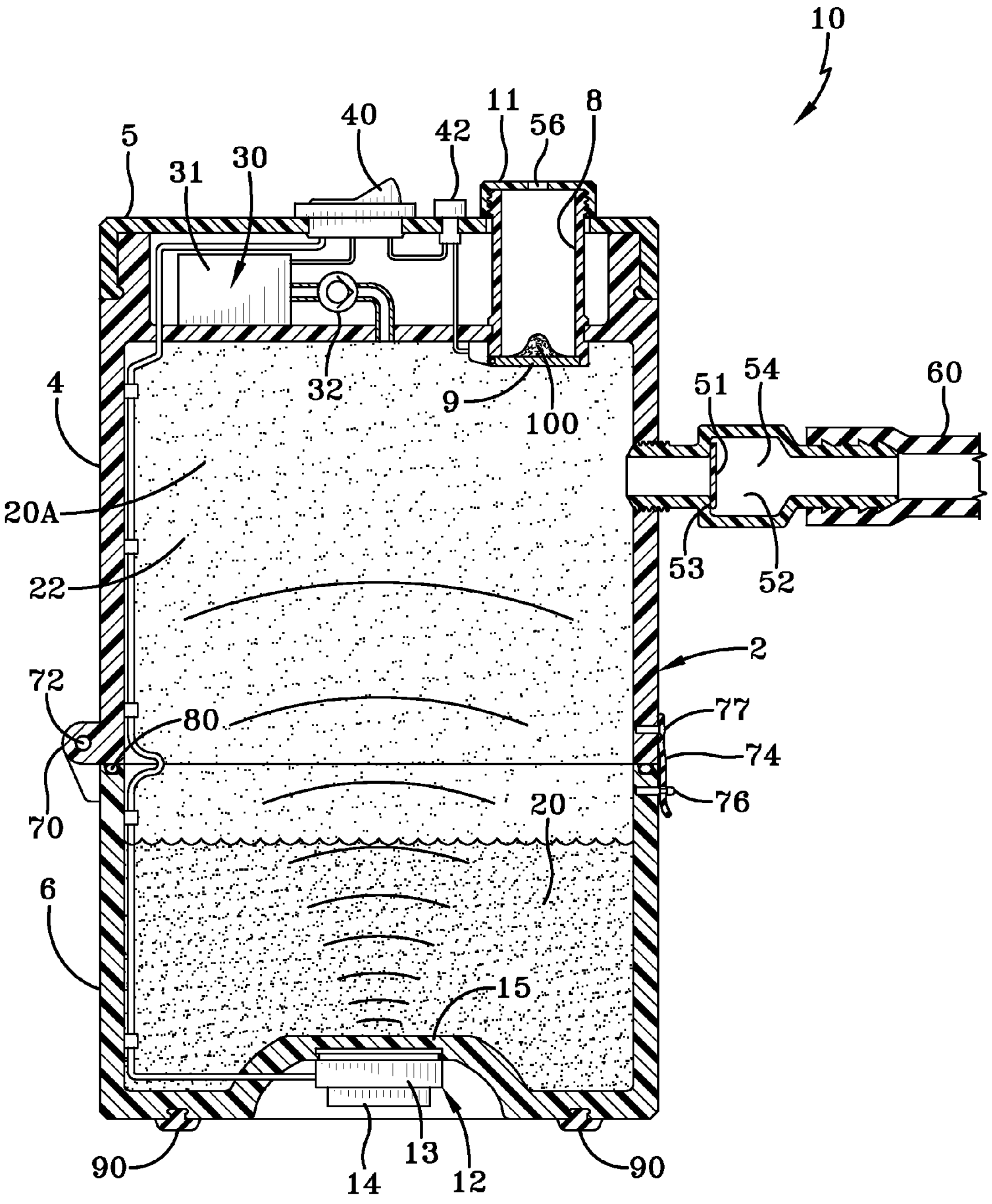
FIG. 2 is a second cross sectional view of the nebulizer of FIG. 1 after activation of the ultrasonic transducer.

A pump means 30 is connected to the primary chamber 4. The pump means 30 has a one way check valve 32 such as a solenoid valve between the pump 31 connection and the primary chamber 4 connection. By depressing a first switch 40 the pump 31 is activated which evacuates some of the air 22 and water vapor 20A mixture of the primary chamber 4 from an initial pressure $P_0$ of ambient or about 14.7 psi to a reduced pressure $P_1$ of less than $P_0$, the pressure $P_1$ being preferably less than 12 psi or between 12 and 7 psi typically, thereafter the ultrasonic transducer 12 is activated for a predetermined time ($t_1$) as shown in FIG. 2. During this time a vapor mist or fog 20A is generated. As the reduced predetermined pressure $P_1$ is achieved the pump means 30 shuts off. The primary chamber 4 is air tightly sealed during this time and the one way check valve 32 prevents further air leakage back flowing through the pump 31.

The movement of the air 22 and water vapor 20A across the valve 32 creates a drop in temperature due in part to the Joule-Thompson Effect. The primary chamber air temperature $T_0$ was initially at ambient and as the pressure drops the temperature correspondingly drops to $T_1$. This is as one would anticipate under the normal equations for a perfect gas $PV=rT$. A drop in pressure from $P_0$ to $P_1$ while the volume remains constant results in a change in temperature from $T_0$ (ambient) to $T_1$ (less than ambient).

Figure 3:
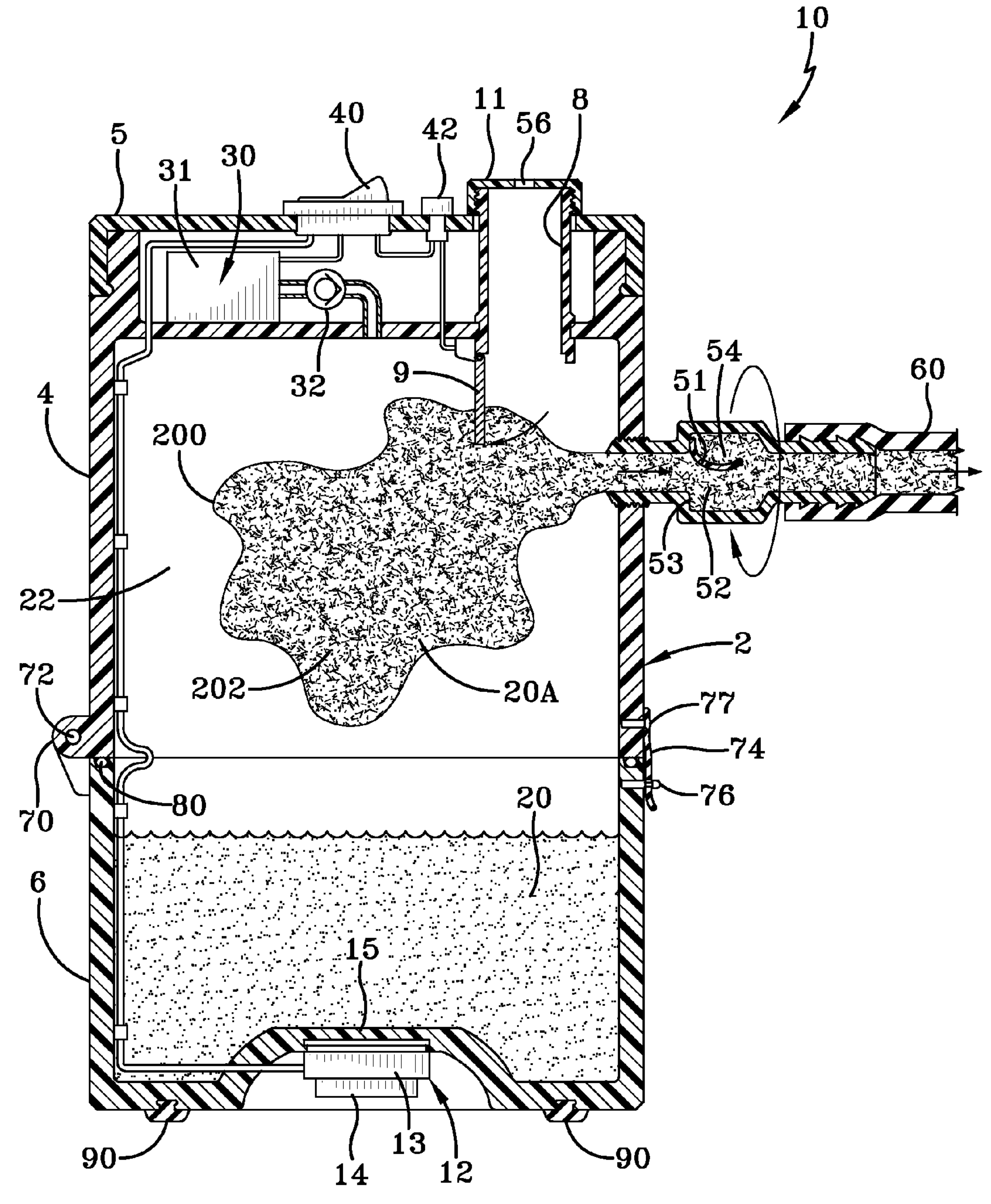
FIG. 3 is a third cross sectional view of the nebulizer of FIG. 1 after the dose of powder medicine is released into the primary chamber.

After the pump means 30 shuts down a second switch 42 automatically or by a manual activation opens the valve or end closure 9 on the medicament dispenser chamber 8 as shown in FIG. 3. This releases a dose of fine powder medicine 100 into the moisture laden mist or fog rich vapor inside the chamber 4. The water vapor molecules 20A attach to the medicine particles of the medicant dosage 100 to produce a cloud 200 of water droplets 202. These droplets 202 are in the size of approximately 2 to 10 microns and thus are maintained suspended in the cloud 200. This is important in that larger droplet sizes tend to condense onto the surfaces of the container and thus would deplete the dosage delivered. The present invention by having the secondary chamber 6 below the primary chamber 4 can rely on gravity to insure larger water droplets fall back into the water volume 20 and to not remain in suspension. Accordingly the fine powder particles of the medicant dosage 100 are attached to the smaller water vapor molecules 20A and remain in a seeded cloud 200 of medication.

As illustrated the cloud 200 can be visible through the primary chamber 4 which is preferably made of a clear plastic material.

A mouthpiece connector 52 is connected to the primary chamber 4. Flap 51 is attached inside the lumen of passageway 54 in an expanded area mouthpiece connector 52 and abuts against a reduced diameter stop 53 to seal the opening during evacuation. As the chamber 4 is already rarefied and filled with water vapor, conditions are satisfied to form a cloud immediately after seeding with the cloud forming powder dosage 100. Along with the entry of the dosage 100, air enters through the vent passage 56 and enters the chamber 4 and the chamber pressure rises to atmospheric allowing the patient to suck on the tubing 60 to unseal the flap 51. Additionally, a vent passage 56 to ambient air located on the cap closure 11 is opened when the end closure or valve 9 opens allowing ambient air to re-enter the primary chamber 4. Accordingly as the patient breathes inhaling the cloud 200 ambient air 22 is allowed into the chamber 4 through the vent opening 56 filling the volume as the cloud 200 is withdrawn and inspired into the patients lungs.

The cloud 200 laden with the dose 100 of medicine is easily transferred with 1 or 2 breaths and thus is received as a bolus inhalation into the lungs. Virtually all of the medicine transfers as the cloud formation 200 insures the medication dosage 100 stays suspended in the very tiny droplets 202 of a size substantially smaller than 120 microns, typically having an average size in the 2 to less than 10 micron size.

The invention as disclosed creates a vapor-rich environment suitable for cloud formation without requiring a separate heating element or a cooling coil to enhance cloud formation.

By using the thermodynamic principles of the ideal or perfect gas law the change in lowering or reduced pressure correspondingly creates a change in temperature lower the temperature of the gases in the primary chamber while the mist of water vapor is being generated by the ultrasonic transducer. As the medication in a fine powder form is dispersed into the water vapor-rich air mixture, the water vapor molecules 20A attach to individual particles of medicine 100 forming the cloud 200 of extremely small size medicine laden water droplets 202 ideally suited for inhalation deep into the lungs. The seeding of the cloud by the introduction of fine powder particles adds mass to the system which correspondingly further reduces the temperature slightly.

This technique avoids the use of heating elements or cooling coils to facilitate the formation of a mist. As can be equally appreciated the use of these added components not only increased cost but were in fact sources of errors in that improper temperature controls or settings actually could render the equipment less efficient causing large percentages of a medication dosage to be condensed into droplets that would adhere to the container or chamber walls without ever reaching the patient. As such a doctor could never be sure if the patient ever received a sufficient amount of the medication.

The present invention by operating in a temperature range closer to room temperature avoids these condensation issues while still providing a suitable environment for cloud formation.

As shown the nebulizer 10 can be formed of two separate chambers, an upper primary chamber 4 and a lower secondary chamber 8. The two chambers are attached by a hinge 70 pivotable about the hinge pin 72. On the opposite side of the hinge a means 74 for closing the nebulizer 10 is shown. The means 74 is attached to the upper chamber 4 by a fastener 77 and securely slips over an attachment pin 76 as shown. An O ring type seal 80 is positioned in a groove on top of the secondary chamber 6 and upon attaching the means 74 for closing the nebulizer forms an airtight seal between the chamber 4 and chamber 6 as shown. This provides for a simple yet efficient way to open and wipe clean the nebulizer 10 after each use.

As further shown the nebulizer preferably has rubber pads 90 on the bottom of the lower secondary chamber 6. These pads 90 keep the nebulizer 10 from vibrating on a hard surface and thus prevent movement and reduced noise.

As shown in the FIGS. 1-3 the transducer 12 is external to the secondary chamber 6. Alternatively the transducer can be mounted internally if so desired. In either way the transducer 12 simply must be capable of producing a vapor-rich atmosphere Similarly the one way check valve 32 can be replaced with a one way solenoid valve 32 and a timer (not shown) which after a predetermined time to evacuate the chamber 4 can be used to activate the switch 42 to automatically open the movable end closure or valve 9 to seed the cloud thereby eliminating the need to manually activate the switch 42.

Although not show it is understood that and is preferable that the nebulizer 10 is powered using batteries that are preferably rechargeable or can be electrically connected to an electrical outlet plug by a cord if so desired. In another alternative construction the end closure 9 may be spring loaded to snap open when the pressure differential of the evacuated chamber meets a required amount. In this case the transducer 12 must be activated sufficiently quickly prior to the pump 30 reaching the evacuated pressure needed to have the spring snaps open. Once opened the end closure 9 must be manually reset to the closed positioned after being used and prior to being reused.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. An unheated nebulizer apparatus for dispersing powdered medicine in a cloud comprising:

an enclosure including a primary chamber of ambient air, a separated vented medicant chamber always vented to the atmosphere during use of the apparatus, the medicant chamber being sealable from the primary chamber and located in an upper portion or top of the enclosure and holding a fine powdered medicine; a secondary chamber containing water in communication with an ultrasonic transducer and in communication with the primary chamber;

a first switch for activating a pump for evacuating air from the primary chamber when activated, the pump being configured to evacuate and extract air from the primary chamber for a predetermined time, the pump when stopped being followed by activation of the transducer for a predetermined time leaving an unheated low pressure vapor-rich atmosphere; thereafter a moveable end closure or valve which opens upon activation of a second switch unseals the medicant chamber relative to the primary chamber allowing a dose of the powdered medicine to drop or fall through the partial vacuum aided by gravity along with an inrush of air and cools and expands the powdered medicine laden unheated low pressure vapor-rich atmosphere of the primary chamber to complete the conditions for seeding and forming a cloud laden with medicine in the absence of any heating or cooling elements; and a mouth piece attached to said primary chamber, the mouth piece sealed during evacuation and unsealed after cloud formation to allow the patient to suck and inhale the medicine laden cloud as a bolus as air vents through the vented medicant chamber into the primary chamber, the cloud being made up of powdered medicine attached to water vapor molecules having a size of 2 to 10 microns to remain suspended in the formed cloud.

2. The apparatus of claim 1 wherein the primary container initially has ambient air at room temperature $T_0$ and atmospheric pressure $P_a$, and the ultrasonic transducer when activated creates a water vapor mist drawn into said chamber after activation of said pump means for evacuating air lowering said primary chamber pressure to $P_1$ and lowering said temperature to $T_1$ less than $T_0$ upon activating said second switch to open the moveable end closure or valve, dropping the powdered medicine into the primary chamber as the powdered medicine seeds and in combination with the water vapor mist forms the medicine laden cloud.

3. The apparatus of claim 1 wherein a one way check valve is mounted between the pump and the primary chamber to prevent loss of the reduced pressure in the primary chamber.

4. The apparatus of claim 3 wherein said enclosure is a transparent or otherwise clear container which enables one to observe the formation of the cloud of vapor and medication.

5. The apparatus of claim 4 wherein said mouth piece is included for inhaling the contents of the primary chamber; and wherein the mouth piece further includes a one way valve means connected to or internal of the mouth piece for forming an open passage from the primary chamber to the patient.

6. The apparatus of claim 1 further comprising a check valve means for preventing reverse flow from said pump back into said primary chamber.

7. The apparatus of claim 1 wherein said moveable end closure or valve when opened is configured to introduce a dose of the powdered medicine by which the powder is dispersed into the primary chamber after the vapor pressure has been adjusted to complete the conditions for seeding the vapor and enhancing cloud formation; the medicant chamber has a cap with a vent and the valve is configured such that when the moveable end closure or valve opens the medicine dosage enters under the pull of the partial vacuum and gravity into the primary chamber and atmospheric air passes through the vent into the primary chamber.

8. The apparatus of claim 1 further comprises:

a screw cap tightly fastened to the medicant chamber, the screw cap having a vent open to atmospheric air.

9. The apparatus of claim 1 wherein the primary and secondary chambers are separate chambers.

10. The apparatus of claim 9 wherein the primary and secondary chambers are attached by a hinge and sealed together to form the enclosure.

11. The apparatus of claim 10 wherein the primary chamber and secondary chamber are sealed by an “O ring” seal.

12. The apparatus of claim 1 further comprising rubber pads affixed to the bottom of the secondary chamber of the enclosure.

13. The apparatus of claim 1 wherein the ultrasonic transducer is located external to the secondary chamber.

14. A method of forming a cloud of water vapor seeded with powdered medicine to form molecules in the size of 2 to 10 microns that can be inhaled to treat the lungs, comprising the steps of:

isolating a liquid within an enclosure after lowering the pressure and temperature within the enclosure to a value of reduced pressure and lower temperature that enhances the subsequent formation of a cloud and ultrasonically vibrating the liquid for a predetermined time to form a vapor mist of the liquid;

arranging a quantity of treatment medicine that is in the form of a finely divided powder held in a separate vented medicant chamber always vented to atmosphere in an upper portion or top of the enclosure, the medicant chamber sealed from the enclosure; said quantity of powder is selected to provide a dose of medicine for one's lungs; thereafter dispersing said dose of medicated powder by dropping the powder from the vented medicant chamber into the enclosure assisted by the partial vacuum along with an inrush of air and gravity, therefore expanding and cooling the unheated and low pressure atmosphere of the vapor mist of liquid to complete the conditions for seeding and forming a cloud laden with medicine, wherein the medicant powder particles in combination with the water vapor molecules having a size of 2 to 10 microns to remain suspended in the formed cloud;

connecting a mouthpiece to the enclosure; and using the mouthpiece to translocate the formed cloud into the lungs; and further including the steps of: placing a one way check valve between a pump means and the enclosure to prevent subsequent loss of the medicated cloud and venting ambient air through the medicant chamber during and after dispersing the powder to facilitate inhaling the cloud as a bolus into the lungs.

* * * * *